United States Patent
Bo et al.

(10) Patent No.: US 10,446,563 B1
(45) Date of Patent: Oct. 15, 2019

(54) PARTIALLY DISPOSED GATE LAYER INTO THE TRENCHES

(71) Applicant: TEXAS INSTRUMENTS INCORPORATED, Dallas, TX (US)

(72) Inventors: Xiang-Zheng Bo, Plano, TX (US); John H. Macpeak, Garland, TX (US); Douglas T. Grider, McKinney, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/945,552

(22) Filed: Apr. 4, 2018

(51) Int. Cl.
| | | |
|---|---|---|
| *H01L 21/00* | (2006.01) | |
| *H01L 27/11521* | (2017.01) | |
| *H01L 29/788* | (2006.01) | |
| *H01L 29/06* | (2006.01) | |
| *H01L 29/49* | (2006.01) | |
| *H01L 29/10* | (2006.01) | |
| *H01L 21/66* | (2006.01) | |
| *H01L 21/311* | (2006.01) | |
| *H01L 21/762* | (2006.01) | |
| *H01L 21/768* | (2006.01) | |
| *H01L 21/28* | (2006.01) | |
| *H01L 29/66* | (2006.01) | |
| *H01L 29/423* | (2006.01) | |
| *H01L 27/02* | (2006.01) | |

(Continued)

(52) U.S. Cl.
CPC .. *H01L 27/11521* (2013.01); *H01L 21/28273* (2013.01); *H01L 21/31111* (2013.01); *H01L 21/76224* (2013.01); *H01L 21/76802* (2013.01); *H01L 21/76877* (2013.01); *H01L 22/20* (2013.01); *H01L 27/0207* (2013.01); *H01L 29/0649* (2013.01); *H01L 29/1083* (2013.01); *H01L 29/42328* (2013.01); *H01L 29/4916* (2013.01); *H01L 29/66825* (2013.01); *H01L 29/788* (2013.01); *G01B 2210/56* (2013.01); *G01N 21/9501* (2013.01); *G03F 7/70625* (2013.01); *H01L 21/26513* (2013.01); *H01L 22/12* (2013.01)

(58) Field of Classification Search
CPC ............ G01N 21/9501; G03F 7/70625; G01B 2210/56; H01L 22/12
See application file for complete search history.

(56) References Cited

U.S. PATENT DOCUMENTS 6,953,697 B1 * 10/2005 Castle .................... H01L 22/12
257/E21.53
7,250,372 B2 * 7/2007 Friedmann .......... H01L 21/0276
257/E21.029

(Continued)

*Primary Examiner* — Nicholas J Tobergte
(74) *Attorney, Agent, or Firm* — Jacqueline J. Garner; Charles A. Brill; Frank D. Cimino

(57) ABSTRACT

In accordance with some examples, a system comprises a substrate layer having an outer surface. The system also comprises a plurality of trenches extending from the outer surface into the substrate layer. The system then comprises a plurality of active regions with each active region positioned between a different pair of consecutive trenches of the plurality of trenches. The system also comprises a dielectric layer disposed in each of the plurality of trenches and on each of the plurality of active regions. The system then comprises a floating gate layer disposed on the dielectric layer and extending at least partially into each of the plurality of trenches.

13 Claims, 13 Drawing Sheets

(51) Int. Cl.
*H01L 21/265* (2006.01)
*G01N 21/95* (2006.01)
*G03F 7/20* (2006.01)

(56) References Cited

U.S. PATENT DOCUMENTS

| | | | | |
|---|---|---|---|---|
| 7,299,105 | B2* | 11/2007 | Holfeld | H01L 22/20 257/E21.525 |
| 7,352,453 | B2* | 4/2008 | Mieher | G01N 21/956 356/125 |
| 7,425,482 | B2* | 9/2008 | Jeong | H01L 27/105 257/315 |
| 7,674,350 | B2* | 3/2010 | Zhuang | H01L 21/32137 156/345.22 |
| 2002/0094639 | A1* | 7/2002 | Reddy | G06K 19/07749 438/257 |
| 2006/0043458 | A1* | 3/2006 | Rudeck | H01L 27/115 257/315 |
| 2008/0157168 | A1* | 7/2008 | Mizukoshi | H01L 21/28282 257/316 |

* cited by examiner

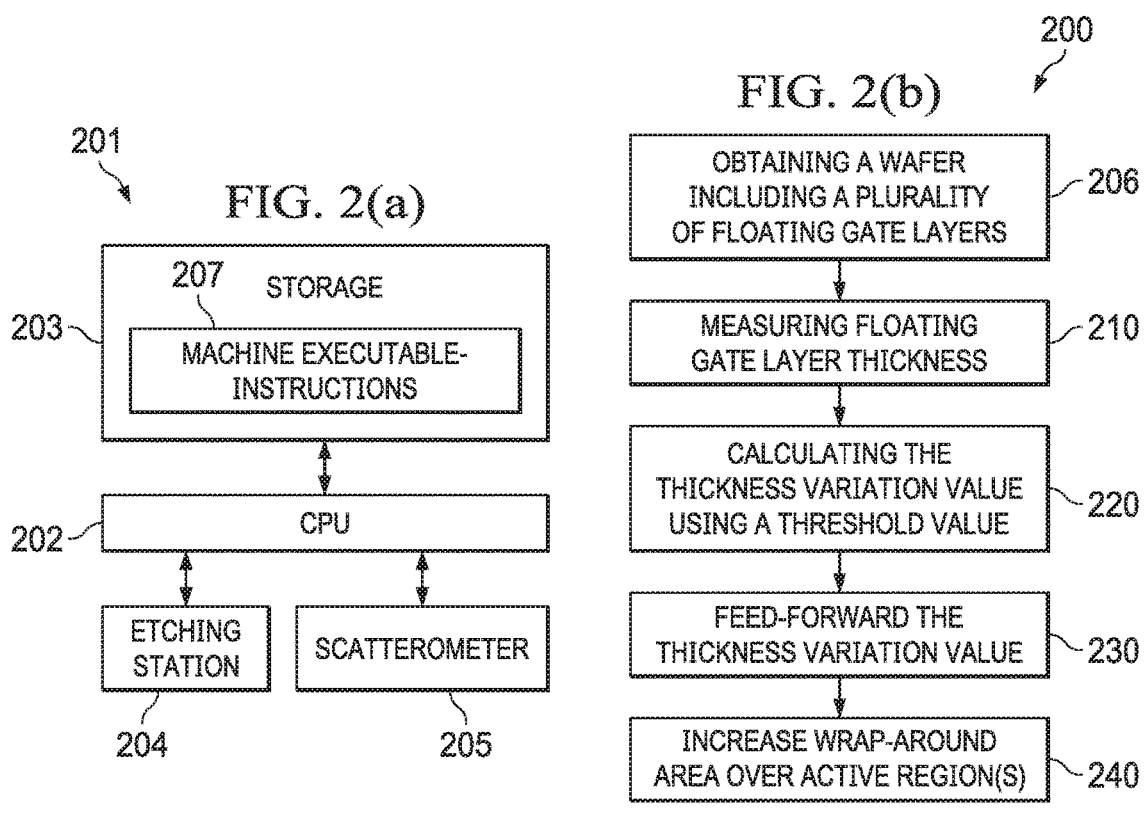
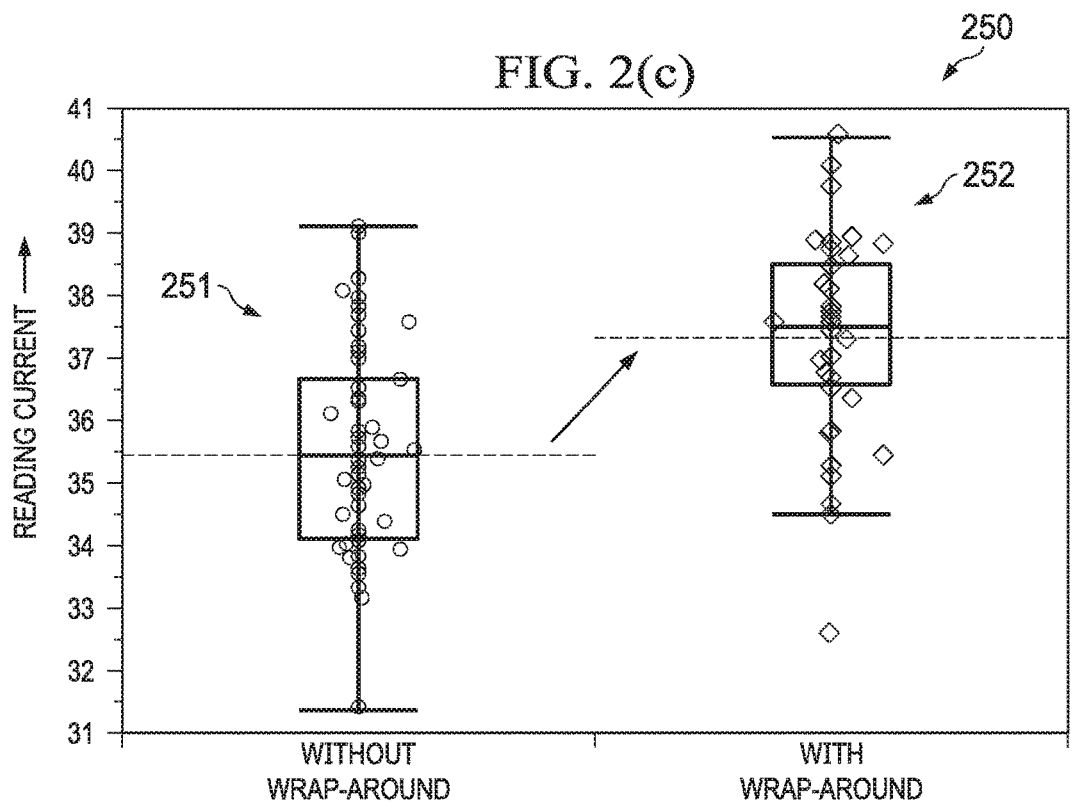

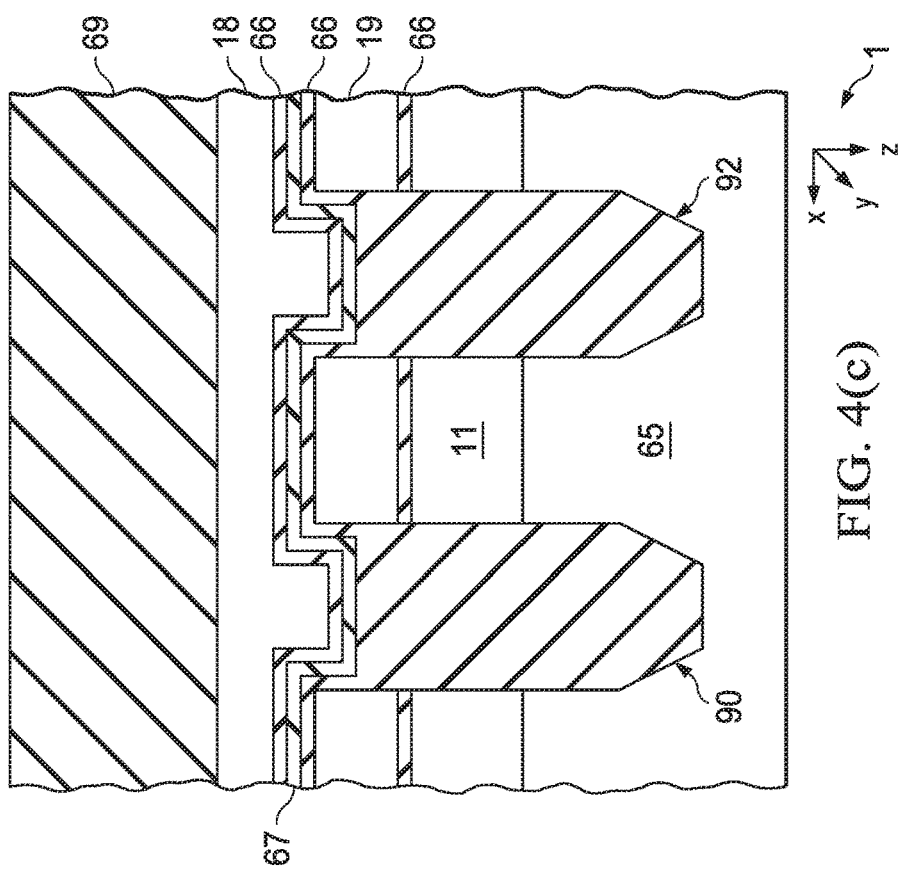
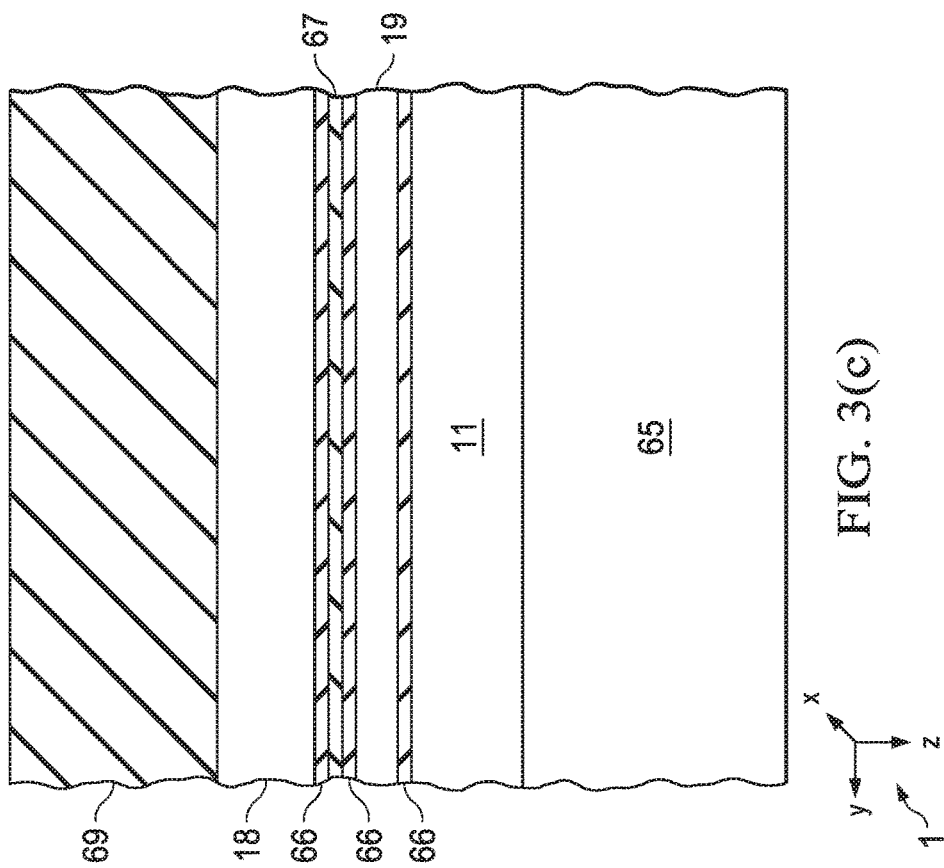

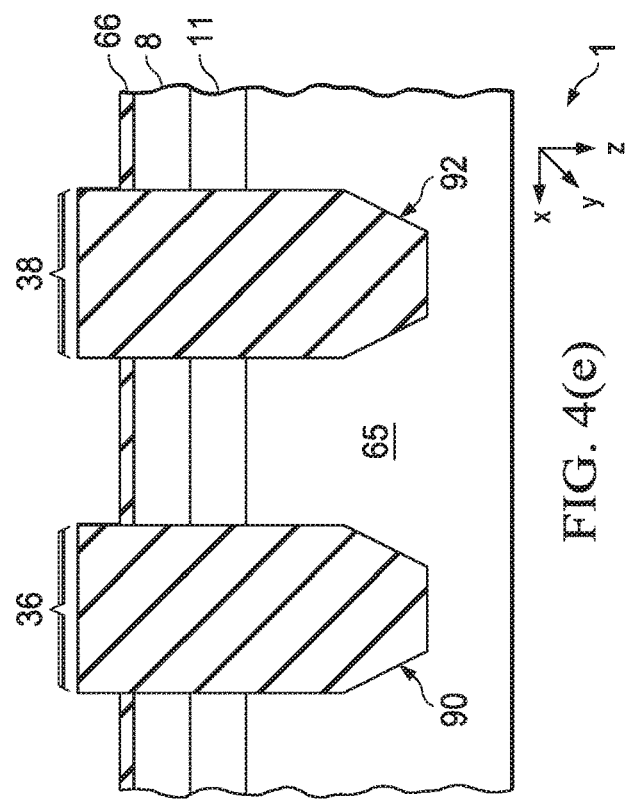
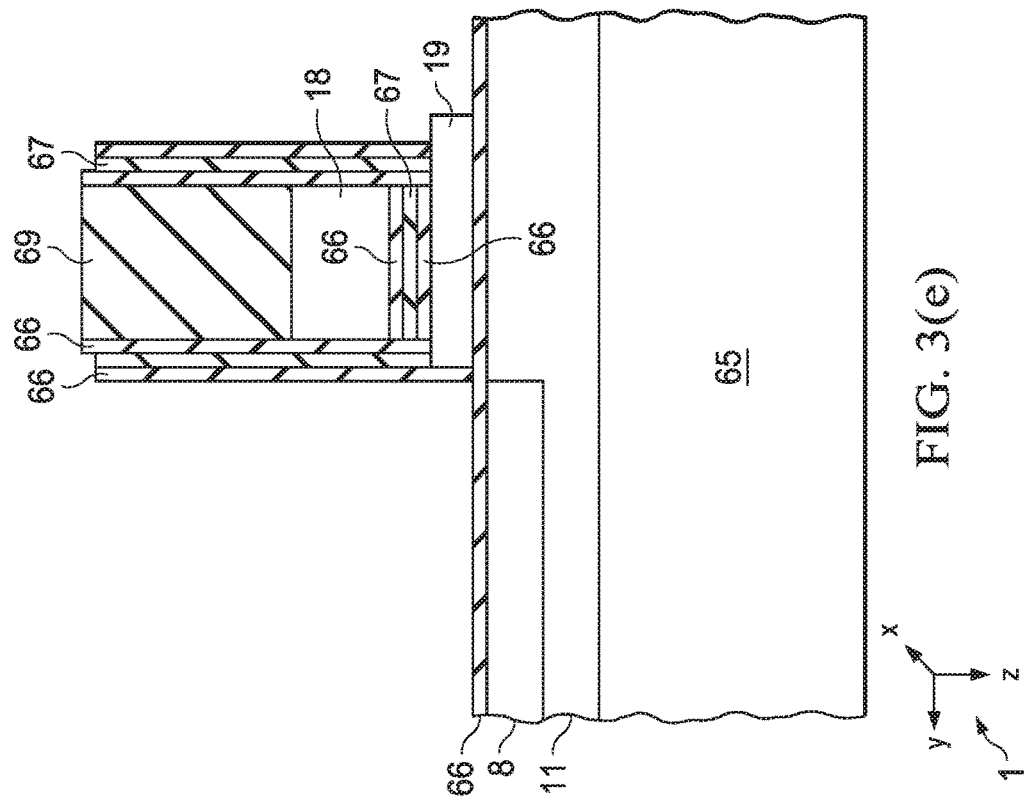
FIG. 3(e)
FIG. 4(e)

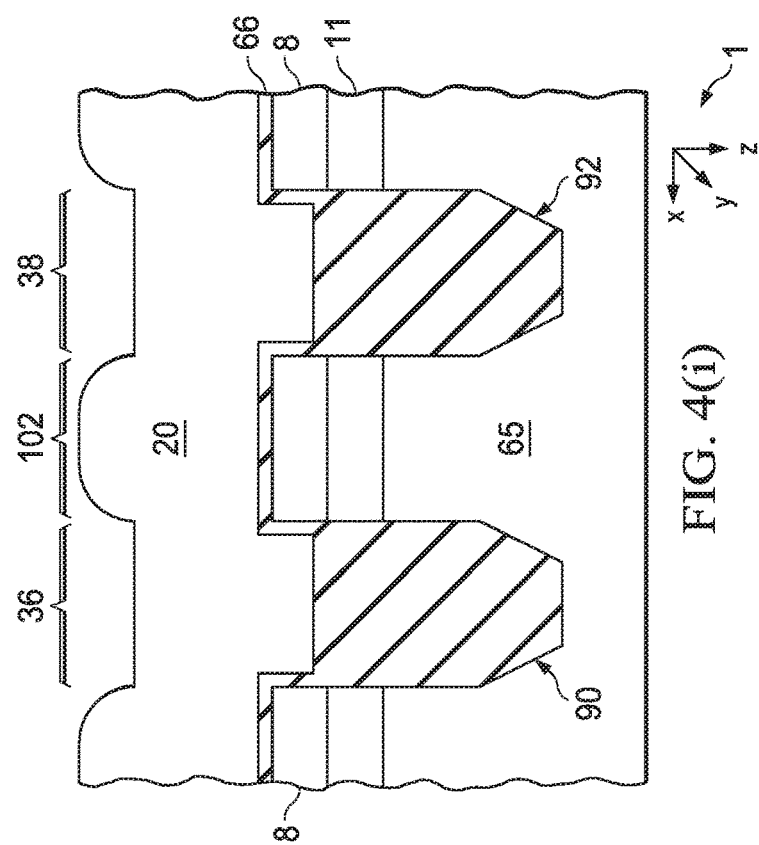
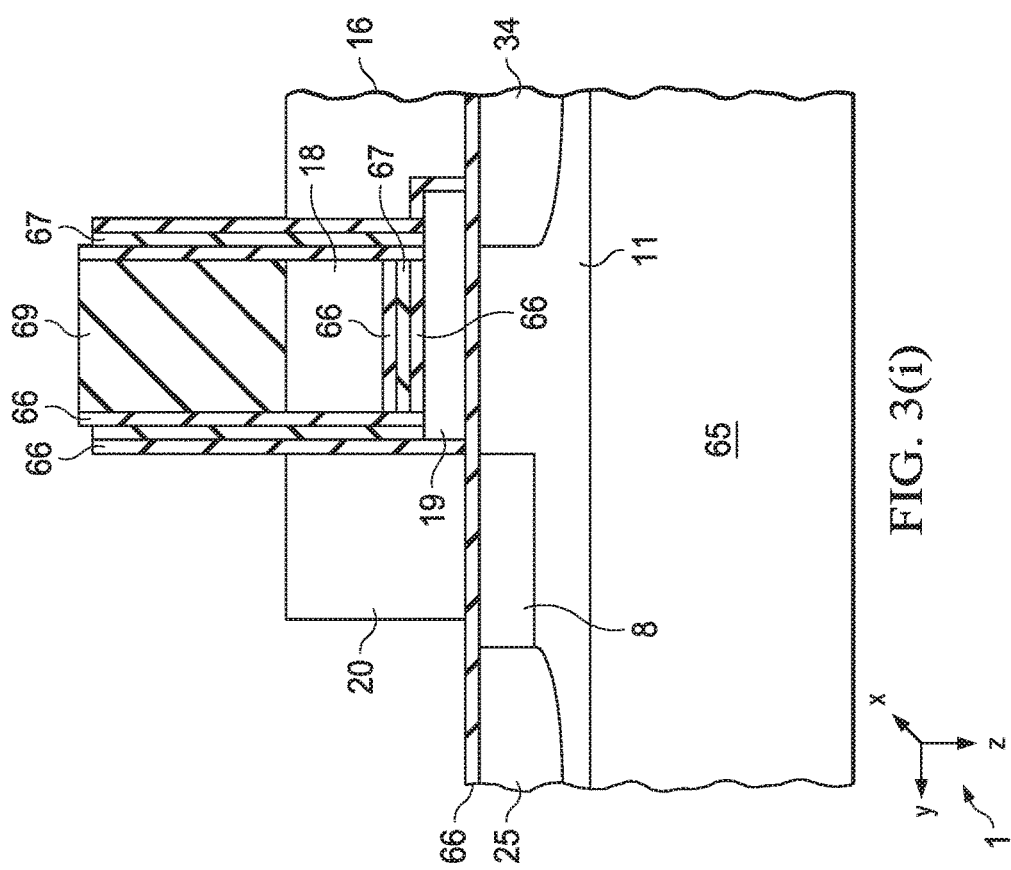
FIG. 4(i)
FIG. 3(i)

PARTIALLY DISPOSED GATE LAYER INTO THE TRENCHES

BACKGROUND

A non-volatile-memory (NVM) bitcell is an electronic element that is configured to store information. The electrical state (e.g., threshold voltage) of a bitcell can be used to define a logic level, such as a logic low level (meaning digital low or 0) or a logic high level (meaning digital high or 1). This defined logic level may sometimes be referred to as information (or a bit) stored in the bitcell.

SUMMARY

In accordance with at least one example, a system comprising a substrate layer having an outer surface. The system also comprising a plurality of trenches extending from the outer surface into the substrate layer. The system also comprising a plurality of active regions with each active region positioned between a different pair of consecutive trenches of the plurality of trenches. The system then comprising a dielectric layer disposed in each of the plurality of trenches and on each of the plurality of active regions. The system also comprising a floating gate layer disposed on the dielectric layer and extending at least partially into each of the plurality of trenches.

In accordance with at least one another example, a method comprising obtaining a wafer including a plurality of floating gate layers; measuring thicknesses of the plurality of floating gate layers; calculating a floating gate thickness variation value using the measured floating gate layer thicknesses and a target value; and increasing, based on the floating gate thickness variation value, an oxide etch time of the wafer.

In accordance with at least yet another example, a method comprising obtaining a substrate layer having an outer surface and comprising a plurality of shallow trench isolation structures extending from a first surface above the outer surface into the substrate layer, wherein a first dielectric layer interfaces with the outer surface, and wherein a plurality of floating gate layers are positioned on the first dielectric layer; measuring a thickness of each of the plurality of floating gate layers; calculating a floating gate thickness variation value using the measured thicknesses of the plurality of floating gate layers with a target value; and etching the plurality of shallow trench isolation structures based on the floating gate thickness variation value.

BRIEF DESCRIPTION OF THE DRAWINGS

For a detailed description of various examples, reference will now be made to the accompanying drawings in which:

FIG. 2(a) depicts an illustrative floating gate feedforward system, in accordance with various examples.

FIG. 2(b) depicts an illustrative method to compensate for the floating gate thickness variation across the semiconductor wafer, in accordance with various examples.

FIG. 2(c) depicts an illustrative graph showing data points of flash memory array reading currents including wrap-around and no wrap-around over the active region, in accordance with various examples.

FIGS. 3(a)-3(i) illustrate fabrication steps for fabricating a bitcell, in accordance with various examples.

FIGS. 4(a)-4(i) illustrate fabrication steps adjusting wrap-around area over an active region, in accordance with various examples.

DETAILED DESCRIPTION

Figure 1A:
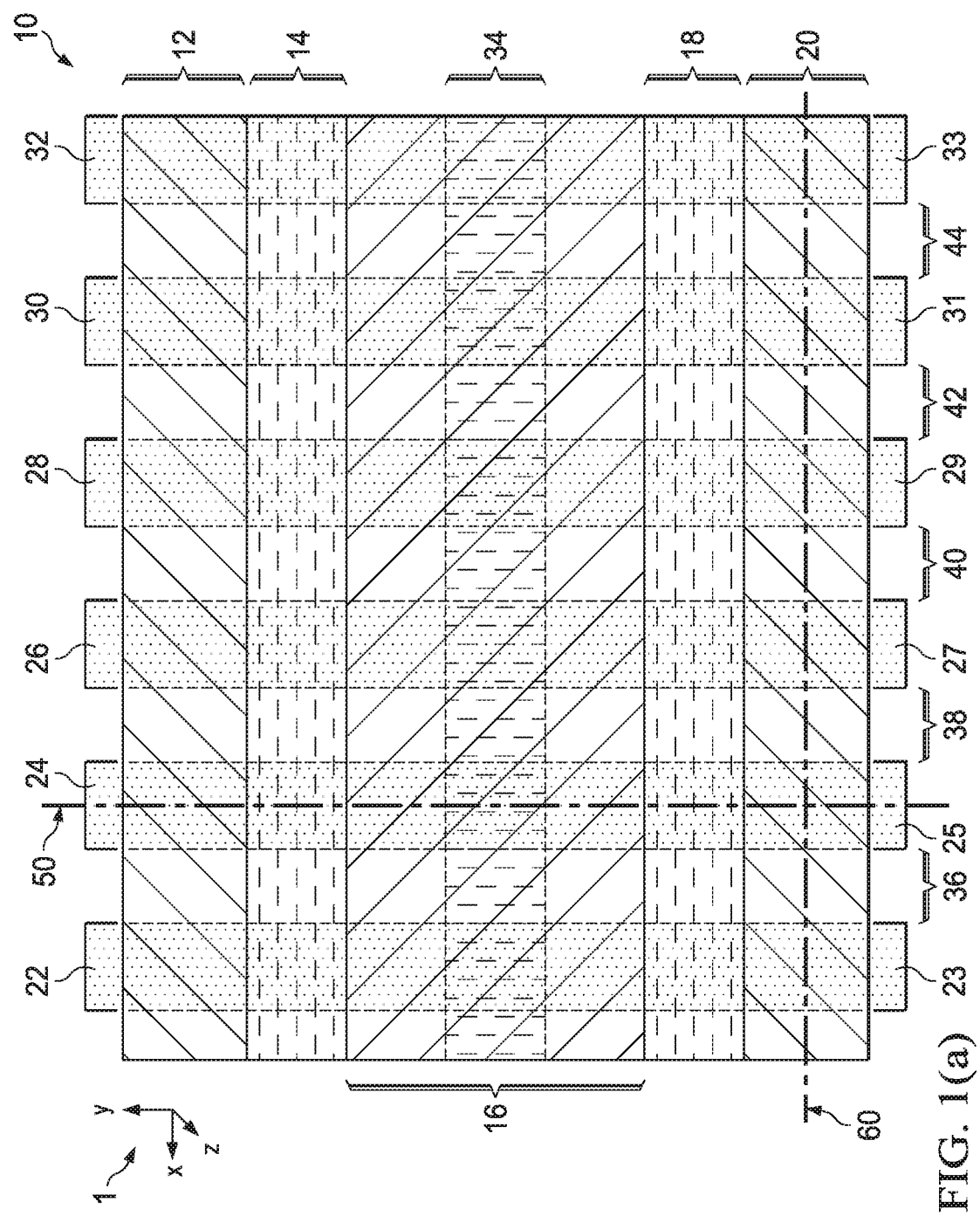
FIG. 1(a) depicts a portion an illustrative layout of a split-gate Flash bitcell memory array, in accordance with various examples.

A flash memory is a non-volatile storage medium that may store information in an array of bitcells. This stored information (or "bit") can be electrically erased, programmed, and read. In some cases, an array of floating-gate transistor bitcells may be used in a flash memory. A floating-gate transistor bitcell resembles a standard metal-oxide-field-effect-transistor (MOSFET), except that the floating-gate transistor bitcell includes multiple gates, e.g., control gate and floating gate. As noted above, an electrical state of a bitcell can be used to define a logic level, which can be further referred to as bit stored in the bitcell. For example, the threshold voltage of a floating-gate type transistor bitcell may increase when electrons are trapped in its floating gate and this different (new) threshold voltage (relative to the base (or old) threshold voltage) can be interpreted as a logic low level. Stated another way, the electrical state present when electrons are trapped in the floating-gate type transistor bitcell can be referred to as a digital low or "0" stored as a bit in the bitcell. On the other hand, the electrical state when electrons are depleted in the floating gate can be referred to as digital high or "1" stored in the bitcell.

In some cases, the floating-gate transistor bitcell utilizes split-gate architecture to store bits. Such a bitcell is typically referred to as split-gate Flash bitcell, which includes more than one transistor. For example, the split-gate Flash memory cell has a portion of the floating gate beneath the control gate, such that the channel of the memory cell transistor is controlled by the word line gate as well as the floating gate. This causes the split-gate Flash memory cell to act two transistors operating in serial, equivalent to 1.5 T per cell, when Source or Drain is shared by two Flash bitcells. Similarly, in some configurations, the split-gate Flash bitcell can have a 2 T (two transistor) configuration. A combination of one or more of these gates can be configured to program, erase, and read the split-gate bitcell.

As noted above, a floating gate in a split-gate Flash bitcell may store a charge (e.g., electrons) and the electrical state of the split-gate Flash bitcell (similar to the floating-gate transistor bitcell) resulting from this charge may be allotted a digital value (0 or 1). For example, the application of a positive voltage potential to the control gate may trap electrons in the floating gate. Such a condition may change the electrical state (e.g., increased threshold voltage) of the split-gate Flash bitcell and this change may represent a logic low level or digital "0" state. Conversely, the absence of electrons in the floating gate may also change the electrical state of the bitcell and such a condition (e.g., reduced threshold voltage) may be represented as a high logic level or digital "1" state.

The electrical state of a split-gate Flash bitcell can be read. This is typically done by reading a current between the bit line and the source line of the bitcell. This reading current is found to be dependent on the thickness of the floating gate. In cases where the floating gate is depleted of electrons (i.e., digital 1 state), the reading current of such "1" state (referred herein as IR1 reading current) may vary significantly due to the floating gate thickness variation. It is also observed that, the thicker the floating gate (with respect to a target thickness), the lower the reading current (and vice versa). From a fabrication standpoint, the floating gate thickness depends on the chemical-mechanical-polishing (CMP) process and/or the subsequent etch-back process. The CMP and etch-back process variation results in floating gate thickness variation between wafers, which consequently introduces a variation in the wafer-to-wafer IR1 reading current.

Traditionally, a source/drain pocket implant is used to compensate for this variation. However, pocket implantation is undesirable because it affects the programming efficiency of the split-gate Flash bitcell. Therefore, a different technique that mitigates the issue of the wafer-to-wafer IR1 reading current variation is desired.

Accordingly, at least some of the examples disclosed herein are directed towards systems and methods for compensating the above-mentioned IR1 reading current variation. In particular, this disclosure describes using a feed-forward process, which compensates for wafer-to-wafer IR1 current variation. As noted above, this wafer-to-wafer IR1 current variation occurs due to the variation of floating gate thickness from a target thickness (e.g., 45 nm). It is observed that increasing the wrap-around area of the word line gate over the active region may increase the IR1 reading current. This disclosure describes a floating gate thickness feed-forward method that includes feed-forwarding a thickness variation value to compensate for the IR1 reading current variation, specifically by increasing the active region wrap-around area of the word line gate layers. At least some of the examples of the floating gate feed-forward method include increasing the wrap-around area of the word line gate layer by increasing the etch time of the isolation regions. In some examples, increasing the etch time may occur in one or more fabrication steps. Stated another way, one or more etching steps may facilitate increasing the wrap-around area of the word line gate layer over the active region. The thickness variation value may be factored in while performing one or more of these etching steps that facilitate increasing the wrap-around area. In some examples, the isolation regions that are etched to increase the wrap-around area may include shallow trench isolation (STI) structures.

Referring now to FIG. 1(a), a portion of an illustrative layout 10 of a split-gate Flash bitcell memory array in accordance with various examples is shown. The layout of the split-gate Flash bitcell memory array depicted in FIG. 1 includes erase gates. However, this disclosure is not limited to a split-gate Flash bitcell memory array including erase gates. The description below is valid for split-gate Flash memory array including word line gates and floating gates.

The layout 10, at least in part, is used as a layout (or blueprint) to fabricate an array of bitcells that are implemented along with a CMOS logic array (not expressly depicted). In some examples, the layout 10 may be used to fabricate an array of bitcells that is implemented as a standalone memory device (e.g., implemented on its own semiconductor die, enclosed within its own chip package, etc.). Other versions are implementable with other devices (e.g., on a die including other devices, enclosed in a chip package that includes other devices, etc.)

The layout 10 depicts at least some of the layers that form an array of split-gate Flash bitcell memory bitcells. The layout 10 includes bit line (BL) layers 22-33 and a source line (SL) layer 34. The layout 10 also includes word line (WL) gate layers 12, 20, erase gate (EG) layer 16, and control gate (CG) layers 14, 18. The layout 10 also depicts regions marked with numerals 36, 38, 40, 42, 44 in which shallow trench isolation structures (not expressly shown) may be positioned. FIG. 1(a) also illustrates a coordinate system 1, where the X-axis and the Y-axis of the coordinate system 1 each lie in the page of the drawing, and the Z-axis lie away from (outwards) the page of the drawing. The coordinate system 1 is illustrated in other figures so that the relative orientations of the various examples are easily ascertained. For example, from a layout 10 perspective, one or more bitcells are positioned on line 50 that is aligned with the Y-axis, however, from a fabrication perspective, a side-view of the cross-section of one or more bitcells may be observed in the Y-Z plane along the line 50. Similarly, from the layout 10 perspective, one or more shallow trench isolation structures may be present along the line 60 that is aligned with the X-axis and from a fabrication perspective, a side-view of the cross-section of the STI regions may be observed in the X-Z plane along the line 60. In some examples, the region between two STI regions is referred to as an active region.

Figure 1B:
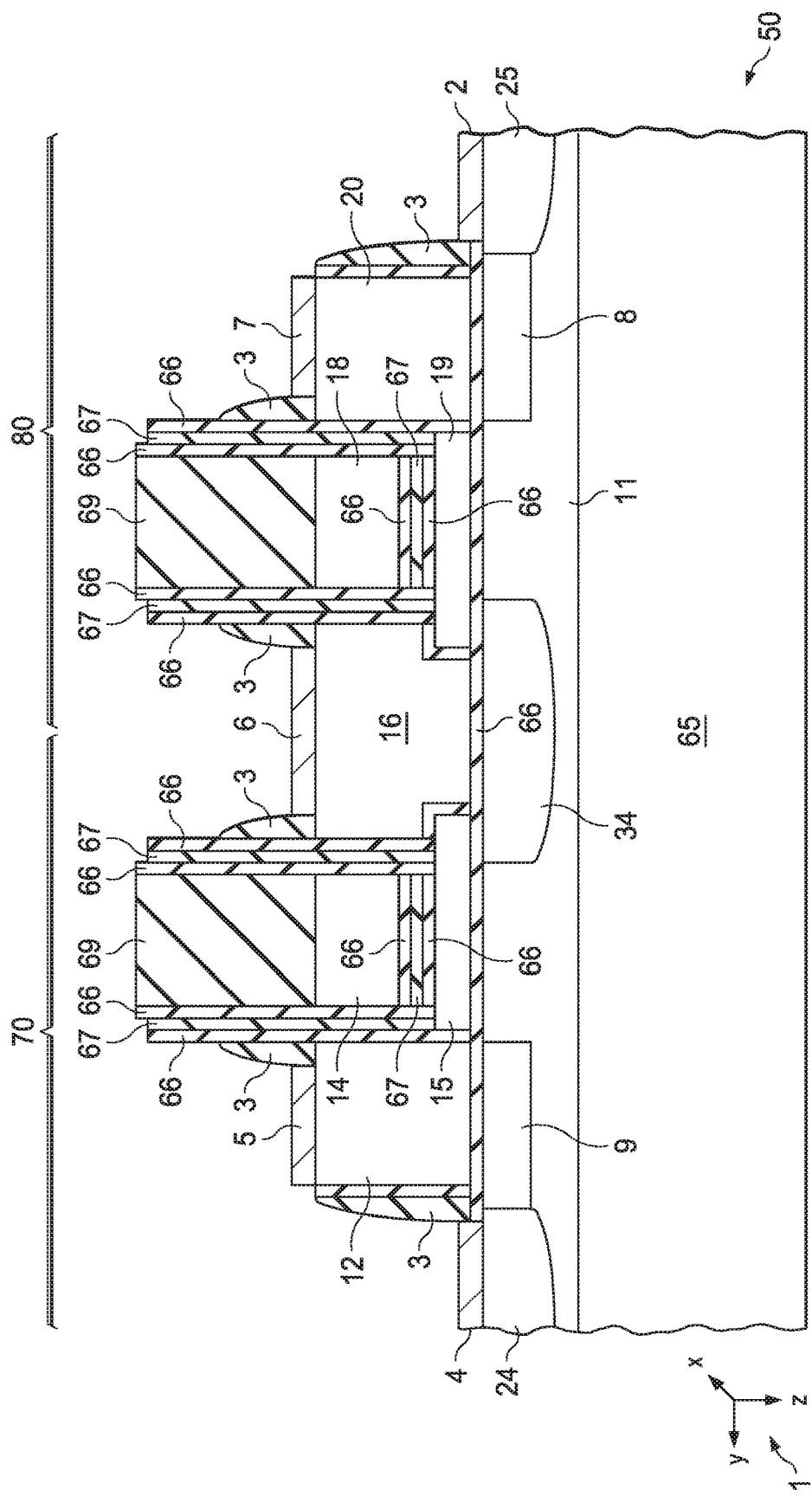
FIG. 1(b) depicts a side-view cross-section of a pair of illustrative bitcells, in accordance with various examples.

Referring now to FIG. 1(b), a side-view cross-section of a pair of illustrative bitcells 70, 80 that may be observed in the Y-Z plane along the line 50. Other bitcells may be observed in the Y-Z plane along with other bit lines that are present on the Y-axis. For example, a pair of bitcells may form along the bit line layers 22, 23, and another pair of bit cells may form along the bit lines 26, 27.

The bitcells 70 and 80 are substantially similar in structure. The bitcell 70 includes the bit line layer 24 that is disposed in the substrate 65. The bitcell 70 also includes the word line gate layer 12, the control gate layer 14, the floating gate layer 15, and the erase gate 16 (that is also shared by the bitcell 80). The bitcell 70 further includes dielectric layers 66, 67, and 69. These dielectric layers are fabricated to provide isolation between the word line gate layer 12, the control gate 14, the floating gate 15, the erase gate layer 16, and the substrate 65. A WL transistor in the bitcell 70 includes the WL gate layer 12 (analogous to a gate of a MOSFET), the bit line layer 24 (analogous to a drain of a MOSFET), and the source line layer 34 (analogous to a source of a MOSFET). The bitcell 70 also includes an implant layer 9 that is disposed below the word line gate layer 12 in the substrate 65. In some examples, the implant layer 9 may be used to alter the threshold voltage of the WL transistor.

Similar to the bitcell 70, the bitcell 80 includes the bit line 25, the source line layer 34, the erase gate 16, the floating gate 19, and the control gate 18. The bitcell 80 also includes dielectric layers 66, 67, and 69, which isolated the erase gate 16, the control gate 18, the floating gate 19, and the word line gate layer 20 from each other. The bitcell 80 also forms a WL transistor that includes the WL gate layer 20 (analogous to a gate of a MOSFET), the bit line layer 25 (analogous to a drain of a MOSFET), and the source line layer 34 (analogous to a source of a MOSFET). In some examples, the substrate 65 may include silicon. In such an example, the dielectric layer 66 may include silicon dioxide and the dielectric layer 67, 69 may include silicon nitride. The bitcell 80 also includes an implant layer 8 that is disposed below the word line gate layer 20 in the substrate 65. Similar to the bitcell 70, the implant layer 8 may be used to alter the threshold voltage of the aforementioned WL transistor.

The bitcells 70, 80 may also include contact layers 2, 4, 5, 6, 7 that are in contact with the bit line layer 25, the bit line layer 24, the word line gate layer 12, the erase gate layer 16, and the word line gate layer 20, respectively. Both bitcells 70 and 80 share the anti-punch through layer 11 that is disposed in the substrate 65. The anti-punch through layer 11 may be used to reduce punch-through leakage between bit line layer 24 and the source line layer 34. This disclosure describes split-gate Flash bitcells including four gates layers (word line gate layer, control gate layer, erase gate layer, and floating gate layer.) The principles discussed herein may be adapted for bitcells including any number of gates (or gate layers).

Figure 1C:
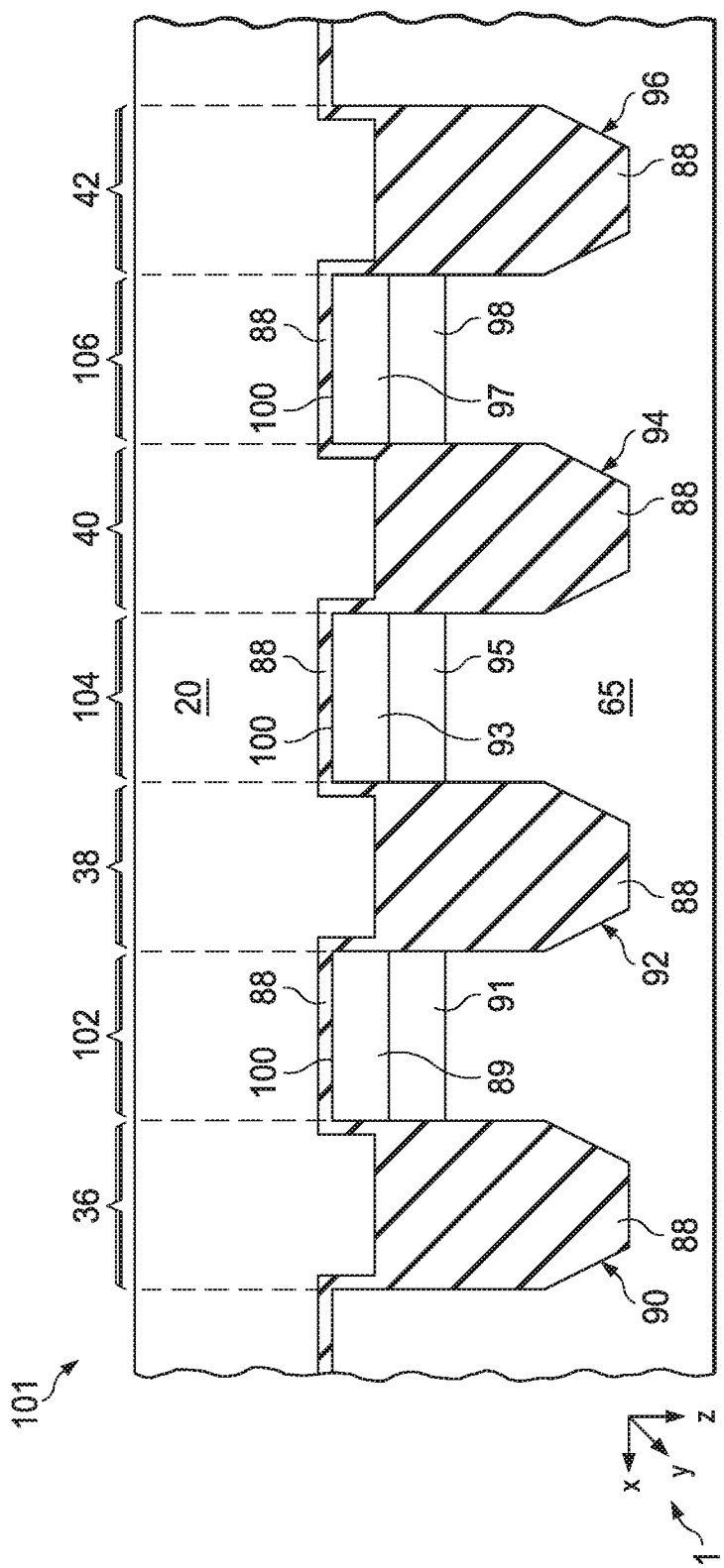
FIG. 1(c) depicts another side-view cross-section of a pair of illustrative bitcells, in accordance with various examples.

As noted above, one or more shallow trench isolation regions may be present along the line 60 (FIG. 1(*a*)) that is aligned with the X-axis. FIG. 1(*c*) depicts a portion 101 along the line 60 that is a side-view cross-section of STI regions that are observed in the X-Z plane along the line 60. FIG. 1(*c*) depicts the regions 36, 38, 40, 42 (FIG. 1(*b*)) in which the shallow trench isolation structures 90, 92, 94, 96 are positioned. FIG. 1(*c*) also depicts the substrate 65 that has an outer surface 100. The portion 101 includes shallow trench isolation structures 90, 92, 94, and 96 that extend from the outer surface 100 into the substrate 65. The portion 101 also includes active regions that exist between two adjacent trenches. For instance, the active region 102 exists between the shallow trench isolation structures 90 and 92. Similarly, the active region 104 exists between the shallow trench isolation structures 92 and 94. The shallow trench isolation structures 90, 92, 94, and 96 include a dielectric layer 88 that extends from each shallow trench isolation structure to an adjacent shallow trench isolation structure over an active region between the two shallow trench isolation structures such that a portion of the dielectric layer 88 is positioned on the active region and the portion serves as the gate oxide layer of the word line gate layer 20.

FIG. 1(*c*) also depicts the WL gate layer 20 that is positioned on the substrate 65 such that the WL gate layer 20 extends partially into each of the shallow trench isolation structures 90, 92, 94, and 96 and is in contact with the dielectric layer 88 disposed in the shallow trench isolation regions 90, 92, 94, and 96 over the active regions 102, 104, and 106. The substrate layer 65, in each of the active regions 102, 104, and 106 includes implant layers. For instance, the substrate 65 underneath the active region 102 includes implant layers 89 and 91. Similarly, the substrate 65 underneath the active region 104 includes implant layers 93 and 95, and the substrate 65 includes, underneath the active region 106, includes implant layers 97, 98. In some examples, the implant layers 89, 93, 97 (similar to the implant layers 8, 9 of FIG. 1(*b*)) may be formed in the substrate 65 by implanting boron, and the implant layers 91, 95, 98 may be the anti-punch through implant layer (similar to the anti-punch through implant layer 11 of FIG. 1(*b*)) and may be formed in the substrate 65 by implanting boron. In some examples, the substrate 65 may be silicon. In such examples, the dielectric layer 88 that is disposed in each of the shallow trench isolation structures may include silicon dioxide and the WL gate layer 20, in such examples, may be polysilicon.

Referring now to the reading operation of the bitcell 80, the information (or bits) stored in the bitcells, such as the bitcell 80, may be read by reading a current between the bit line 25 and the source line 34. Based on the electron density in the floating gate 19, the bitcell 80 can be in the programmed "0" state or eased "1" state. As noted above, the erased bitcell reading current IR1 is dependent on the thickness of the floating gate 19 and the higher the floating gate thickness (relative to a target thickness), the lower the IR 1 reading current (and vice versa.) For example, assume that the desired thickness is 45 nm and the floating gate 19 have a floating gate thickness of 50 nm, and the floating gate 19, due to its higher-than-desired floating gate thickness will exhibit lower IR1 reading current. To compensate for this variation of the IR1 reading current, the word line wrap-around area of the corresponding word line gate layer 20 over the active region 102 is increased.

It can be deduced from FIGS. 1(*a*) and 1(*b*) that the shallow trench isolation structure 92 (that is in the region 38) is positioned behind (i.e., into the drawing towards X-axis per the coordinate system 1) the bitcell 80. To compensate for a thickness variation of the floating gate 19, the wrap-around area of the corresponding word line gate layer around the active regions may be increased. For example, assume that the thickness of the floating gate 19 is higher than a target (or threshold) thickness. In that case, the word line gate layer 20 will have a higher wrap-around in the active region 102 to compensate for the higher thickness of the floating gate 19. Therefore, to compensate for this variation, a higher wrap-around area of the word line gate 20 over its corresponding active region 102 is desired. A higher word line gate layer 20 wrap-around area over the active region 102 can be obtained by increasing the fabrication etch time of the shallow trench isolation structure 92. The description above, for simplicity's sake, is directed to a single bitcell, e.g., bitcell 80. The aforementioned description can be adapted to compensate for wafer-to-wafer variation of IR1 reading current. For example, assume that the desired thickness is 45 nm and the floating gates disposed in a first wafer ("wafer A") have a median floating gate thickness of 50 nm, and the floating gates disposed in a second wafer ("wafer B") have a median floating gate thickness of 55 nm. The wafer A and wafer B, due to its higher-than-desired floating gate thickness will exhibit lower IR1 reading current, and also exhibit different IR1 reading current relative to each other. To compensate for this wafer-to-wafer variation of the IR1 reading current, the word line wrap-around area over the active is increased.

Referring now to FIG. 2(*a*), an illustrative floating gate feedforward system 201 is able to dynamically change the etching time of the shallow trench isolation structures based on the thickness variation value of the floating gate layers present on a wafer. The floating gate feedforward system 201 may be installed in the fabrication processing facility that is fabricating bitcells. The floating gate feedforward system 201 may include a central processing unit (CPU) 202 that is coupled to storage 203 (e.g., random access memory (RAM), read-only memory (ROM)), which may include any suitable type of non-transitory computer-readable medium storing machine-executable instructions, such as instructions 207. The CPU 202, upon executing the instructions 207, performs some or all of the actions attributed herein to the floating gate feedforward system 201. In some examples, the CPU 202 may couple to an etching station 204 that controls the oxide etch time of the wafer based on the thickness variation of floating gate layers as detected using a scatterometer 205 or other suitable measuring device. For example, based on the floating gate thickness measurements received from the scatterometer 205, the CPU 202 may determine the variation in thickness across the floating gate and may control the etching station 204 to increase or decrease the time the wafer is kept in an etch bath accordingly. The more time the wafer spends in the etch bath, the more the oxide will etch, and vice versa. Controlling etch time in this manner impacts the aforementioned wrap-around area over the active regions, thereby compensating for the non-uniform floating gate layer thicknesses.

In some examples, the CPU 202 comprises a cognitive computing system with a neurosynaptic hardware architecture and machine-executable instructions that facilitate machine learning and probabilistic algorithms. The CPU 202 may be a monolithic CPU 202 (e.g., a single device), or it may comprise multiple, separate components, or it may comprise a distributed CPU 202 that is located in multiple, separate locations. The CPU 202 may comprise multiple different sub-systems, including computer sub-systems and non-computer sub-systems (e.g., hardware to perform actions with tangible objects). The CPU 202 may perform its functions in a fully autonomous manner, or it may perform its functions in a semi-autonomous manner (e.g., with human assistance).

Referring now to FIG. 2(b), an illustrative method 200 may be performed to compensate for the floating gate thickness variation across a semiconductor wafer and/or between one or more semiconductor wafers. To summarize, in some examples, first the floating gate thickness variation in a single wafer is determined—for example, using measurements from the scatterometer 205 (FIG. 2(a)). Next, the floating gate thickness variation information as determined using the measurements from the scatterometer 205 is used to adjust the wrap-around area of word line gate layers over active regions of all the bitcells present in the wafer (e.g., by increasing or decreasing the etching time of the shallow trench isolation structure).

Accordingly, FIG. 2(b) depicts an illustrative floating gate feed-forward method 200. The method 200 is now described in tandem with FIG. 3(a)-3(i) and FIG. 4(a)-4(i). The method 200, in conjunction with FIG. 3(a)-3(i) and FIG. 4(a)-4(i), describes the floating gate feed-forward method of a plurality of bitcells present on a wafer. However, for simplicity's sake, FIG. 3(a)-3(i) and FIG. 4(a)-4(i) depicts the fabrication steps of the bitcell 80 (FIG. 2(b)).

Figure 4A:
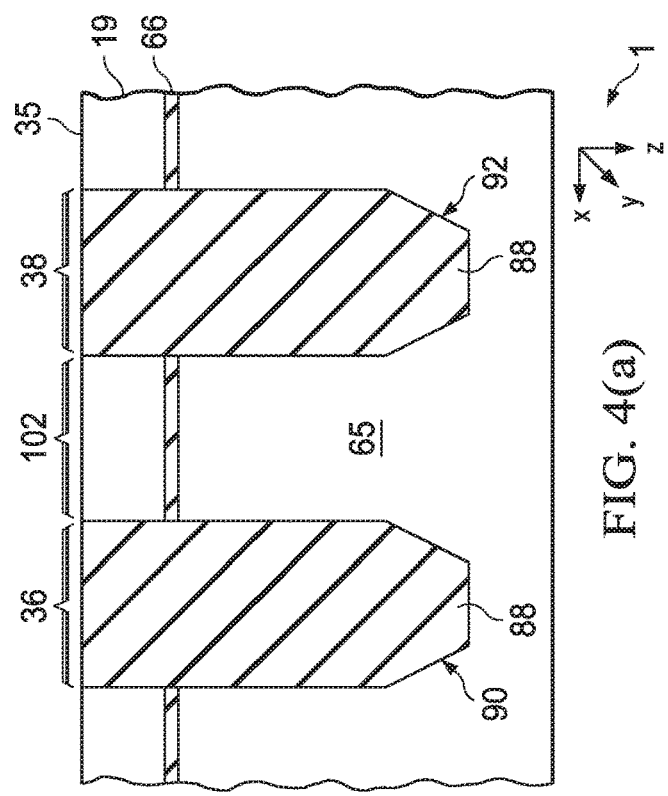

The method 200 may be performed after performing a chemical-mechanical-polishing (CMP) process and/or the etch-back process (not expressly shown). The CMP and etch-back process self-aligns the floating gate layer 19 to the top of the shallow trench isolation structures 90, 92, as depicted in FIG. 4(a). Following the aforementioned self-alignment process, the wafer including a plurality of floating gate layers is obtained (step 206). The wafer may also include a plurality of shallow trench isolation structures and therefore a plurality of floating gate layers self-aligned with the shallow trench isolation structures. The thickness of one or more floating gate layers (such as floating gate layer 19; FIG. 4(a)) may be measured (step 210). In some examples, thickness measurements may be performed using a scatterometer 205. In other examples, different equipment may be used. As noted above, the scatterometer 205 may be coupled to the CPU 202 that is configured to instruct the scatterometer 205 to measure thicknesses of the floating gate layer.

In some examples, the thickness may be measured at different positions across the wafer, which can be further used to find the mean value (or other value, such as median value) of the thickness. For example, the scatterometer 205 may calculate thicknesses of the floating gate at 21 different locations across the wafer. The thickness information from these 21 different locations may be used to determine a mean value of the thickness. The method 200 may further use this calculated mean value and find a thickness variation value by comparing the mean value with a pre-defined target value (step 220). This step 220 may also be performed in the CPU 202 connected to the scatterometer 205. In other examples, a standalone CPU may be present in the scatterometer 205 that can calculate the thickness variation relative to the pre-defined target value. The method 200 may then feed-forward the thickness variation value (step 230) to the CPU 202 that may control the etching time of the shallow trench isolation structures. For example, assume that the CPU 202 (after receiving scatterometer data) compares the mean value of the scatterometer data with the target value and conclude that the mean thickness is higher than the target value. Based on this determination, the CPU 202 may direct the etching station 204 to increase the oxide etching time (e.g., etching time of the shallow trench isolation structures) that may facilitate increasing the wrap-around area of the word line gate layer over the active regions (step 240). Refer briefly to FIG. 4(g), which depicts the etched shallow trench isolation structures 90, 92. The higher the etching time, the deeper the hollow well inside the shallow trench isolation structures 90, 92. Following the aforementioned etching step, word line gate layer 20 may be deposited such that a portion of the word line gate layer 20 is disposed inside the shallow trench isolation structures 90, 92. This partial disposition of the word line gate layer 20 in the shallow trench isolation structures 90 92 increases the wrap around area of the word line 20 over the active region 102, which may compensate for the variation (e.g., increased) in the floating gate layer 19.

FIG. 2(c) depicts an illustrative graph showing data points of flash memory array reading currents that includes a wrap-around (data points 251) over a plurality of active regions. The graph 250 also shows flash memory array reading current data points that include a wrap-around (data points 252) over a plurality of active regions. The data points for the bitcell without wrap-around over active regions reveals a median reading current at ~35.5 uA (data points 251) and the data points for the bitcell including a wrap-around over active regions reveals the median reading current at ~37.5 (data points 252), thus depicting a 2 uA increase in the reading current.

FIGS. 3(a)-3(i) and FIGS. 4(a)-4(i) illustrate fabrication steps that may be used to fabricate a bitcell (e.g., bitcell 80) and compensate for the floating gate layer (e.g., floating gate 19) thickness variation by increasing the wrap-around area of the corresponding word line gate layer (e.g., word line gate layer 20) over the respective active region (e.g., region 102). FIGS. 3(a)-3(i) depict illustrative steps that may be observed in the Y-Z plane (along line 50; FIG. 1(a)) and FIGS. 4(a)-4(i) depict illustrative steps that may be observed in the X-Z plane (along line 60; FIG. 1(a)). For simplicity's sake only one bitcell and its corresponding floating gate layer, word line gate layer, and active region is depicted in FIGS. 3(a)-3(i) and FIGS. 4(a)-4(i). But as noted above, the description below may be adapted for a plurality of floating gate layers, a plurality of bitcells, and the plurality of their corresponding word line and active regions.

In some examples, the substrate 65 may include silicon. In such an example, the dielectric layer 66 may be silicon dioxide and the floating gate layer 19 may include polysilicon.

Figure 3A:
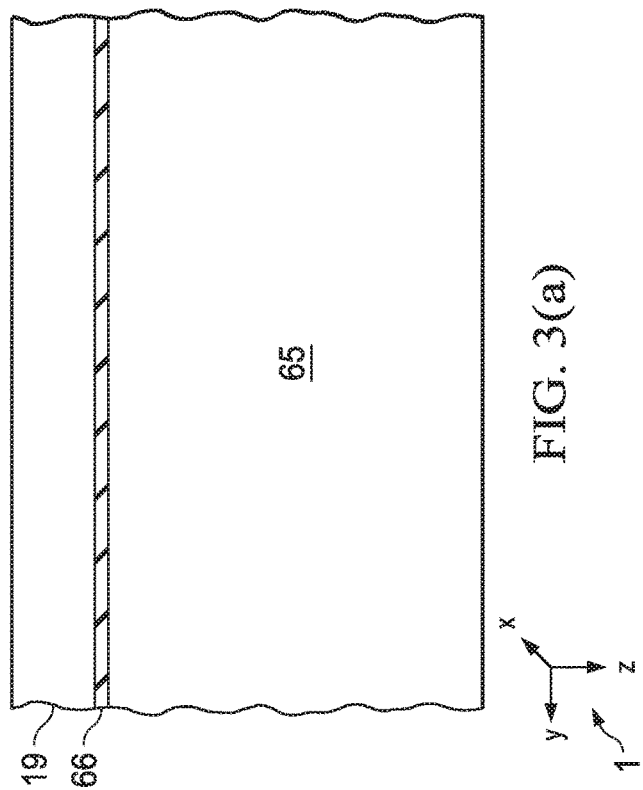

As described above, the thickness of the floating gate layers may be higher or lower than the target thickness c following the self-alignment process and FIG. 3(a) and FIG. 4(a) depicts one such floating gate layer 19. FIG. 3(a) also depicts the substrate 65, the dielectric layer 66. FIG. 4(a) also depicts the substrate 65, dielectric layer 66 (or 88), the shallow trench isolation structures 90, 92, and the floating gate 19 that is aligned with the top of shallow trench isolation structures 90, 92 along the line 35. Stated another way, the shallow trench isolation structures 90, 92 extend from the line 35 into the substrate 65.

Figure 4B:
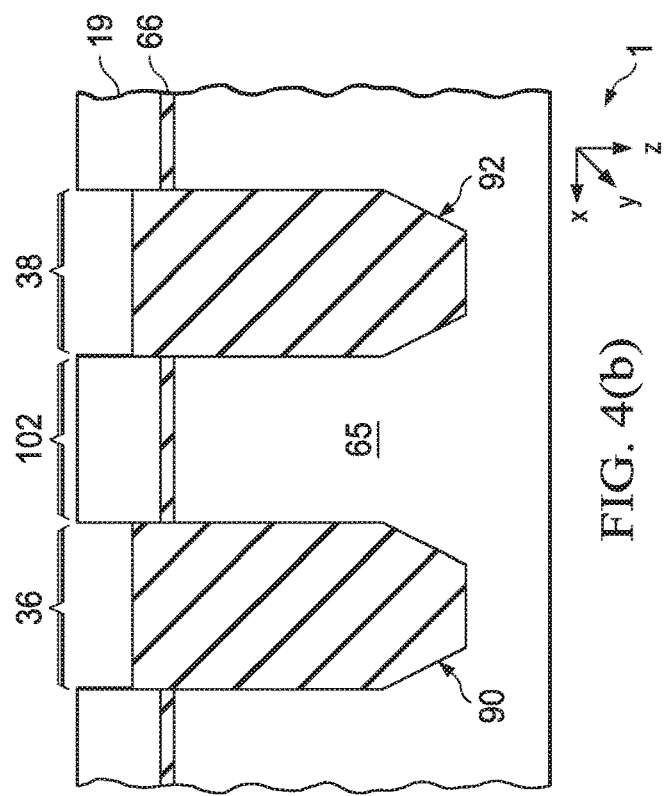
Figure 3B:
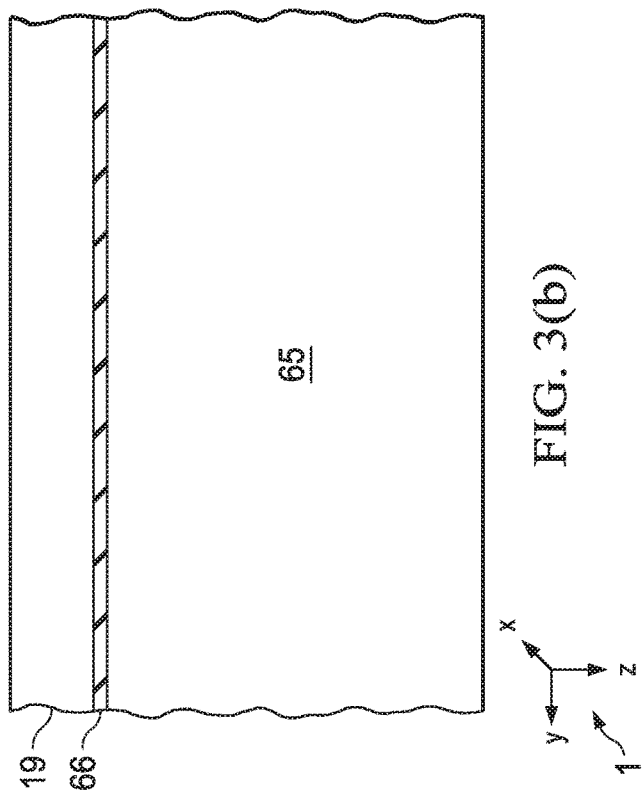

FIG. 4(b) depicts a recess that may be created in the shallow trench isolation structures 90, 92, at least partially based on the thickness variation value calculated above. FIG. 3(b), on the other hand, depicts a substantially similar structure as FIG. 3(a). This may be because the etching step performed to create the recess (depicted in FIG. 4(a)) did not have an effect in the Y-Z plane.

FIGS. 3(c) and 4(c) depict the next steps in the fabrication process following etching the shallow trench isolation structures 90, 92. FIGS. 3(c) and 4(c) depict the formation of cell punch-through implant layer 11 from both the X-Z plane and the Y-Z plane perspectives, respectively. FIGS. 3(c) and 4(c) also depict additional dielectric layer (66, 67) deposition over the floating gate layer 19. FIGS. 3(c) and 4(c) further depict the deposition of control gate layer 18 and the dielectric layer 69 over the control gate layer 18. The dielectric layers 67, 69, in some examples, may include silicon nitride, and the dielectric layer 66 may include silicon dioxide. In some examples, the aforementioned disposition steps may be performed by chemical vapor deposition.

Figure 4D:
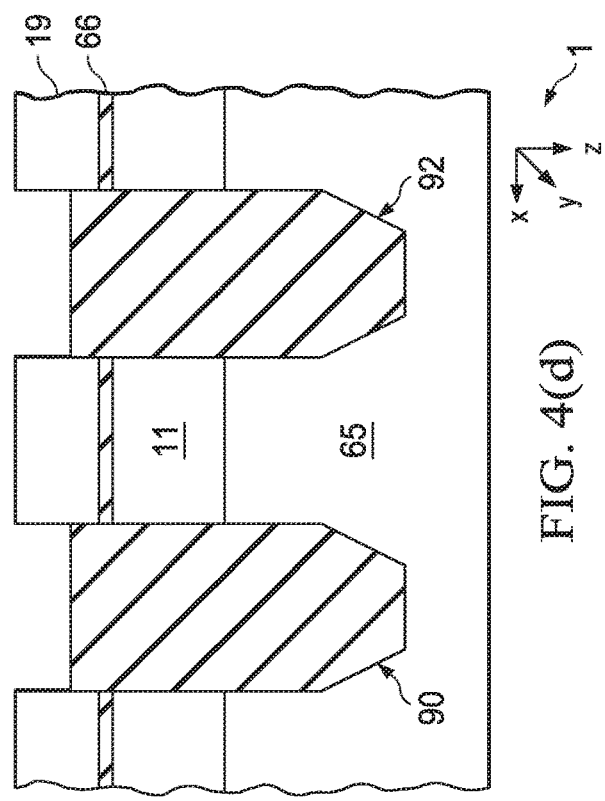
Figure 3D:
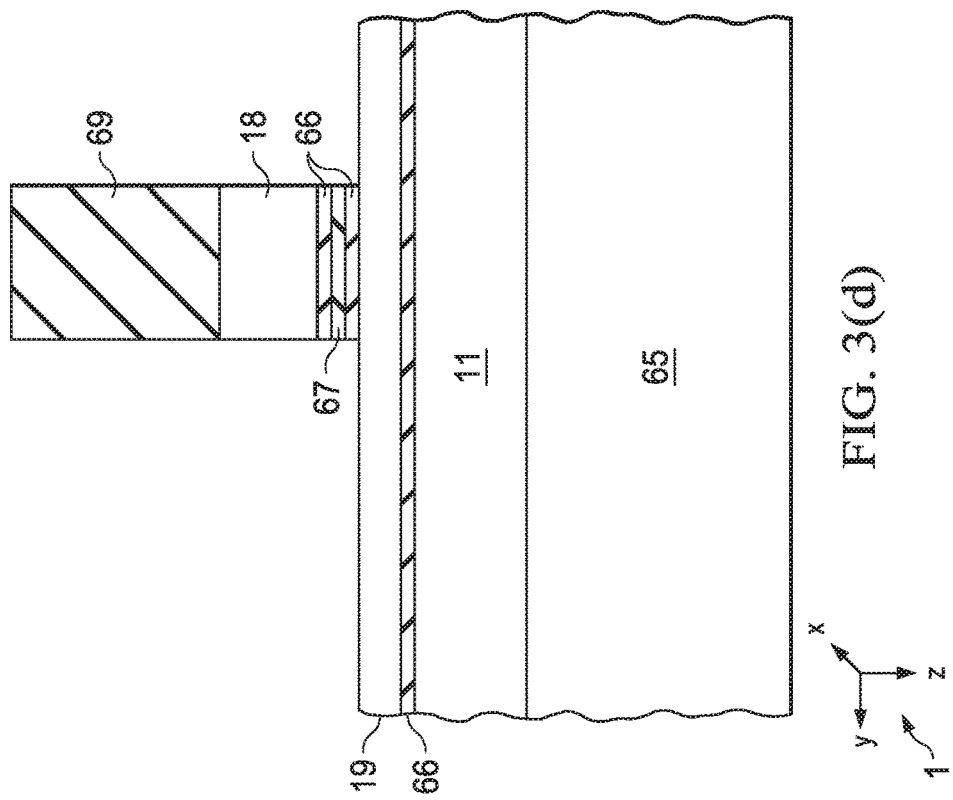

FIG. 3(d) further depicts partial formation of a bitcell stack. FIG. 3(d) depicts the patterned control gate layer 18 and the dielectric layers 66, 67, 69 positioned over the control gate layer 18. FIG. 4(d) depicts a similar structure as depicted in FIG. 4(b).

FIG. 3(e) and FIG. 4(e) depicts the patterned floating gate layer 19. In some examples, at this stage of the fabrication process, another implant layer 8 may be formed in the substrate 65. This implantation may be carried out by using ion implantation technique (or any other related technique). The implant layer 8 is depicted in both FIGS. 3(e) and 4(e). FIG. 4(e) depicts partially etched (due to the etching performed in FIG. 4(b)) shallow trench isolation layer structures 90, 92.

Figures 3F, 4F:
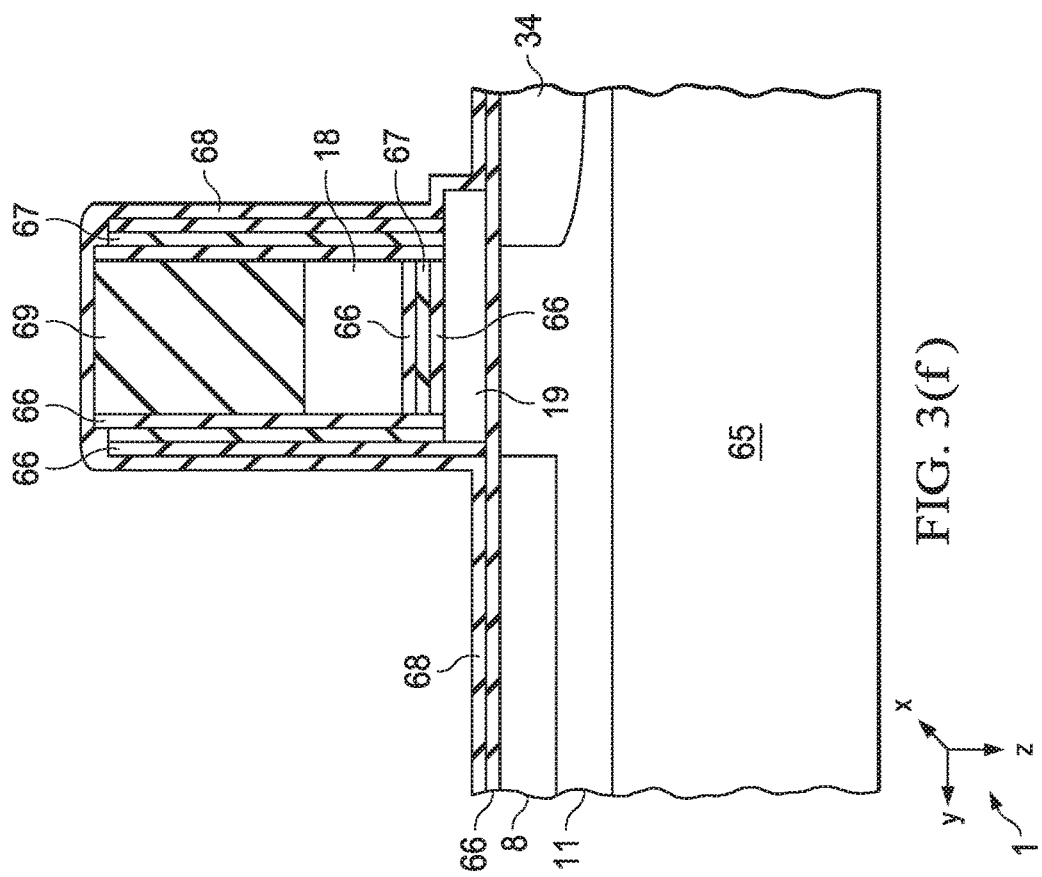
Figures 3G, 4G:
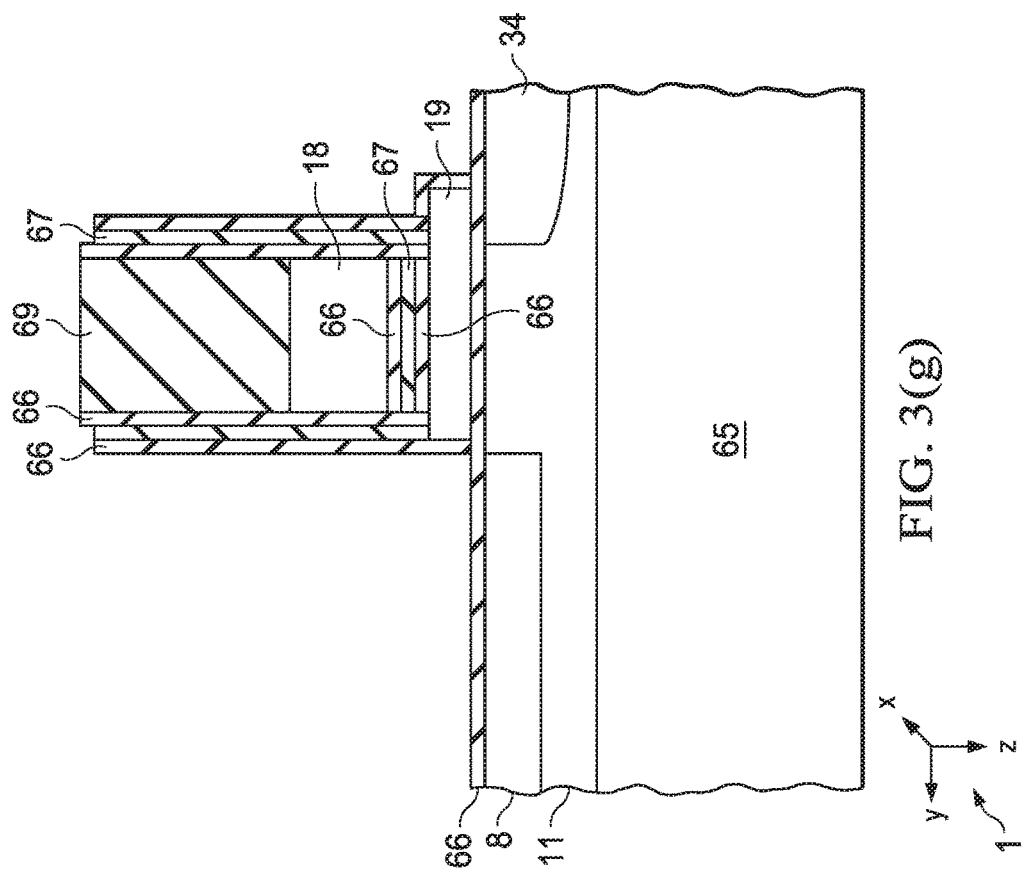
Figure 4H:
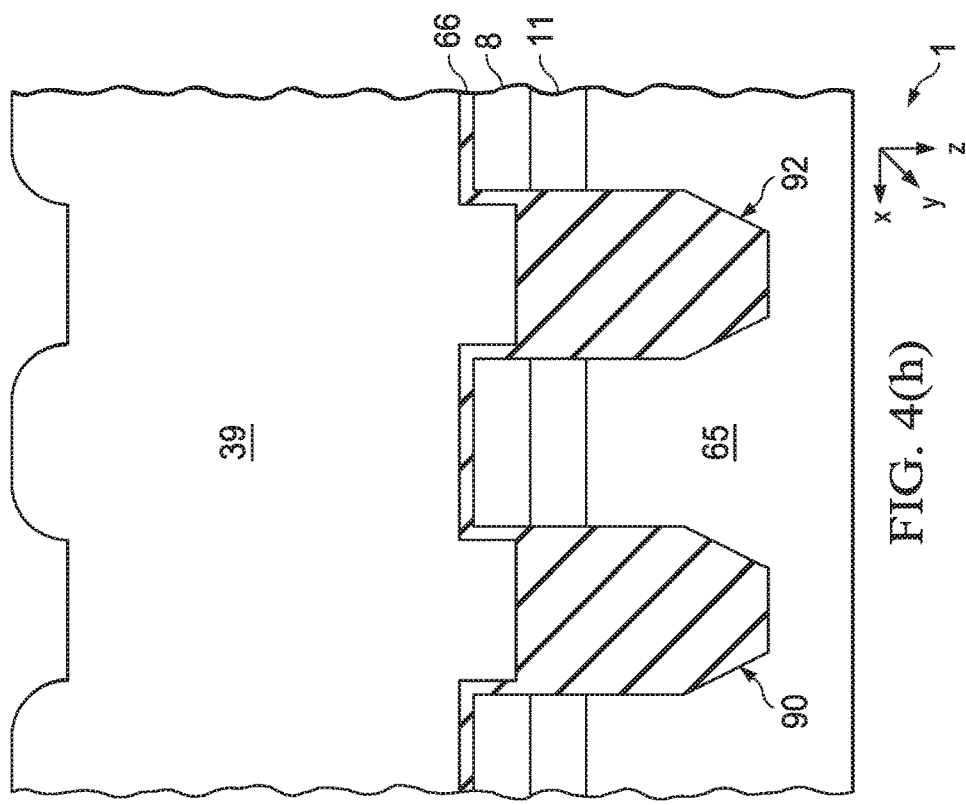
Figure 3H:
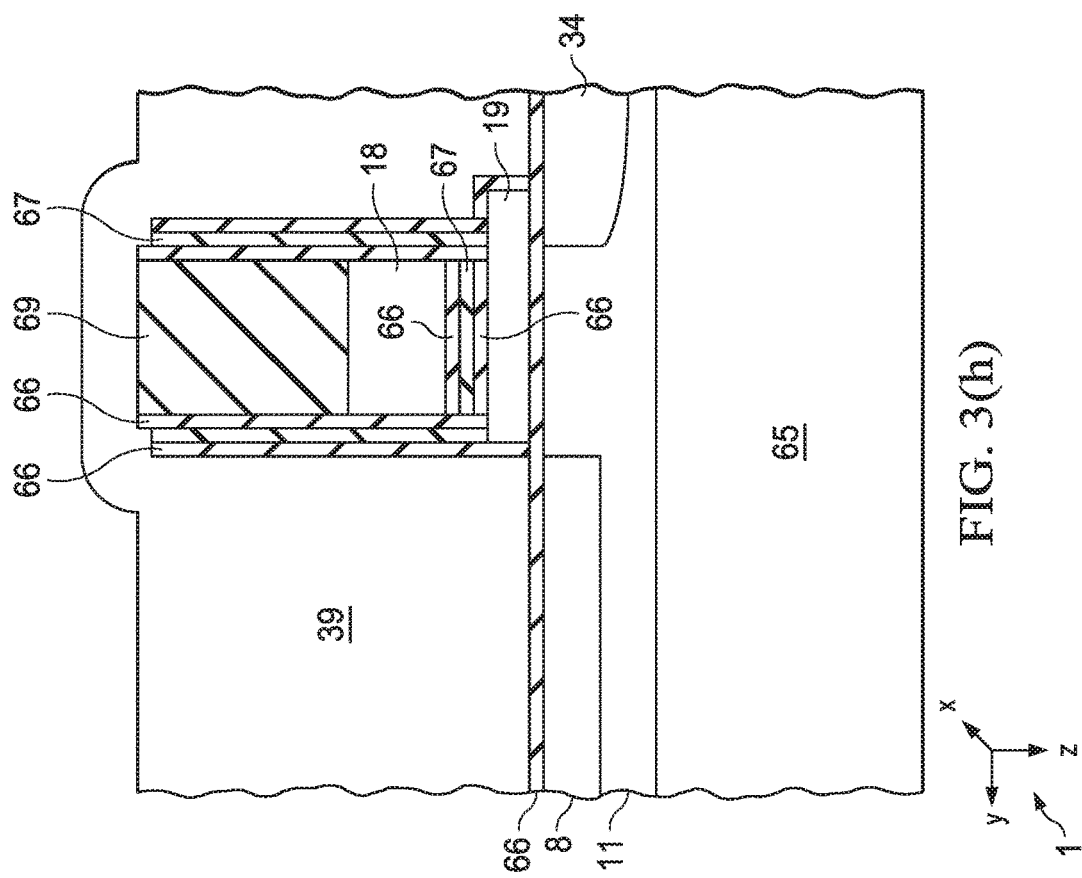

FIGS. 3(f) and 4(f) depict an additional dielectric layer 68 (sometimes referred to as a gap oxide layer) formed over the dielectric layer 66 (in both FIGS. 3(f) and 4(f)). FIG. 3(f) also depicts the source line layer 34, which may be formed using ion implantation. In some examples, both dielectric layer 66 and 68 may include silicon dioxide, and therefore may be referred to as a single dielectric 66. As noted above, the shallow trench isolation structures 90, 92 may be etched at different positions across the fabrication chain. Assume briefly that the shallow trench isolation structures 90, 92 were not etched in FIG. 4(b). In such a scenario, the thickness variation value may be used in FIG. 4(f) to etch shallow trench isolation structures 90, 92 so as to increase the wrap-around area over active regions 36, 38 as depicted in FIG. 4(g). FIG. 4(g) depicts the recess created in the shallow trench isolation regions 90, 92 partially based on the aforementioned thickness variation value. FIG. 3(g) depicts a similar structure as FIG. 3(f), but with a reduced thickness of the dielectric layer 66. FIG. 3(h) and FIG. 4(h) depicts an additional polysilicon layer 39. The polysilicon layer 39 may be deposited using chemical vapor deposition technique. FIG. 4(h) depicts the partially disposed polysilicon layer 39 inside the depicted in FIG. 4(g). FIG. 3(i) and FIG. 4(i) depicts patterned polysilicon layer 39. Following the patterning, the polysilicon layer 39 may transform into word line gate layer 20 and the erase gate layer 16. FIG. 4(i) depicts similar structure as FIG. 3(g), but with a patterned polysilicon layer 39, which is referred to the word line gate layer 20. This word line gate layer 20, partially disposed in the shallow trench isolation structures 36, 38 increases the wrap-around of the word line gate layer 20 over the active region 102, which further compensates for the reading current variation due to the thickness variation of the floating gate layer 19.

In the foregoing discussion and in the claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections.

The above discussion is meant to be illustrative of the principles and various examples of the present invention. Numerous variations and modifications will become apparent to those skilled in the art once the above disclosure is fully appreciated. It is intended that the following claims be interpreted to embrace all such variations and modifications.

What is claimed is:

1. A method, comprising:
    obtaining a wafer including a plurality of floating gate layers;
    measuring thicknesses of the plurality of floating gate layers;
    calculating a floating gate thickness variation value using the measured floating gate layer thicknesses and a target value;
    etching, at least in part based on the floating gate thickness variation value, a plurality of shallow trench isolation structures; and
    increasing, based on the floating gate thickness variation value, an oxide etch time of the wafer.

2. The method of claim 1, wherein measuring the thicknesses of the plurality of floating gate layers using a scatterometer.

3. The method of claim 1, wherein, in response to increasing the oxide etch time of the wafer, increasing a wrap-around area of a plurality of word line gate layers in the plurality of shallow trench isolation structures.

4. The method of claim 1 further comprising depositing a plurality of word line gate layers such that the plurality of word line gate layers partially extend into each of the plurality of shallow trench isolation structures.

5. A method, comprising:
    obtaining a substrate layer having an outer surface and comprising a plurality of shallow trench isolation structures extending from a first surface above the outer surface into the substrate layer, wherein a first dielectric layer interfaces with the outer surface, and wherein a plurality of floating gate layers are positioned on the first dielectric layer;
    measuring a thickness of each of the plurality of floating gate layers;
    calculating a floating gate thickness variation value using the measured thicknesses of the plurality of floating gate layers with a target value; and
    etching the plurality of shallow trench isolation structures based on the floating gate thickness variation value.

6. The method of claim 5 further comprising increasing etching time of the plurality of shallow isolation structures based on the floating gate thickness variation value.

7. The method of claim 5 further comprising depositing a plurality of gate layers such that the plurality of gate layers partially extend into each of the plurality of shallow trench isolation structures.

8. The method of claim 7 further comprising patterning each of the plurality of gate layers to form a plurality of word line gate layers.

9. The method of claim 5 further comprising depositing the plurality of gate layers based on the measured thicknesses of the plurality of floating gate layers.

10. The method of claim 5 further comprising forming a plurality of active regions between two consecutive shallow trench isolation structures.

11. The method of claim 10, wherein the substrate layer, in each of the plurality of active regions, comprises at least one implant layer.

12. The method of claim 5, wherein the substrate layer comprises silicon, the plurality of floating gate layers comprises polysilicon, and the first dielectric layer comprises silicon dioxide.

13. The method of claim 12, wherein the floating gate thickness variation value includes a mean value of the measured thicknesses.

\* \* \* \* \*